United States Patent [19]

Bonati et al.

[11] Patent Number: 5,269,797
[45] Date of Patent: Dec. 14, 1993

[54] CERVICAL DISCECTOMY INSTRUMENTS

[75] Inventors: Alfred O. Bonati, New Port Richey; Philip Ware, Spring Hill, both of Fla.

[73] Assignee: Meditron Devices, Inc., Hackensack, N.J.

[21] Appl. No.: 758,013

[22] Filed: Sep. 12, 1991

[51] Int. Cl.$^5$ ............................................. A61B 17/32
[52] U.S. Cl. ................................... 606/170; 606/174; 606/184; 30/212; 604/22; 128/751
[58] Field of Search ............... 606/168, 170, 171, 174, 606/184, 166; 128/752, 753, 751; 30/211, 212, 213, 214, 231, 232, 234, 235; 604/22; 81/321, 322, 323, 329

[56] References Cited

U.S. PATENT DOCUMENTS

| | | | |
|---|---|---|---|
| 2,112,873 | 4/1938 | Wright | 81/322 |
| 2,532,141 | 11/1950 | Barkan et al. | 81/322 |
| 3,921,640 | 11/1975 | Freeborn | 606/174 |
| 4,499,899 | 2/1985 | Lyons, III | 606/170 |
| 4,712,545 | 12/1987 | Honkanen | 606/184 |
| 4,881,550 | 11/1989 | Kothe | 606/170 X |
| 4,990,148 | 2/1991 | Worrick, III et al. | 606/170 X |

FOREIGN PATENT DOCUMENTS 2457862 7/1975 Fed. Rep. of Germany ...... 128/753

Primary Examiner—Edgar S. Burr
Assistant Examiner—Christopher A. Bennett
Attorney, Agent, or Firm—Joseph C. Mason, Jr.; Ronald E. Smith

[57] ABSTRACT

Arthroscopic cervical discectomy instruments include a push knob for a guide wire, a pair of telescopically mounted dilator tubes, one of which includes a water port so that the tube provides the additional function of an irrigation tube, a ligament cutter, a continuous suction punch, a cervical osteotone, a cervical cureet, a nucleus extractor and a cureet nucleus extractor. The dilator tubes, the ligament cutter, and the continuous suction punch are all centrally bored to receive the guide wire. All of the instruments are of arthroscopic proportions and each instrument, exclusive of its handle, is slidably insertable through the bore of the largest in diameter dilator tube. The largest in diameter dilator tube serves as a dilator, an irrigation tube, and as the main sheath through which the other tools are inserted.

3 Claims, 4 Drawing Sheets

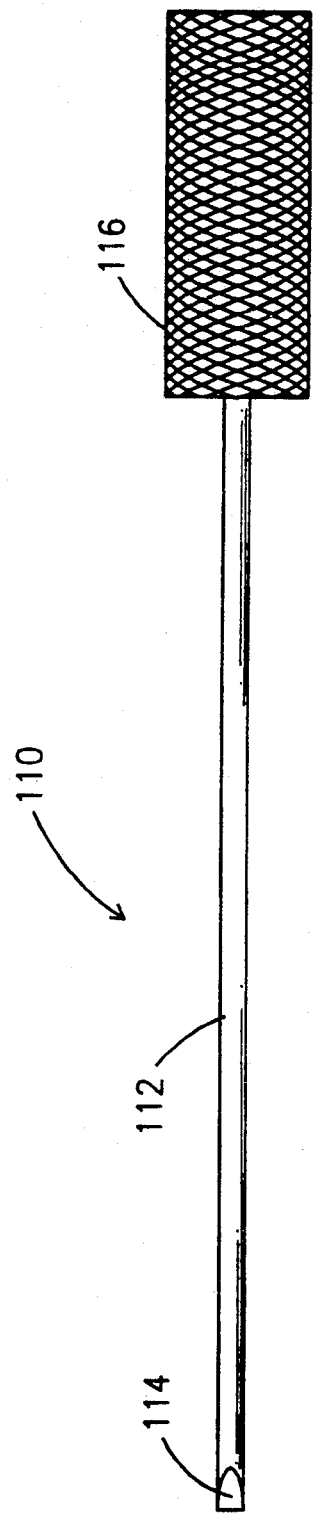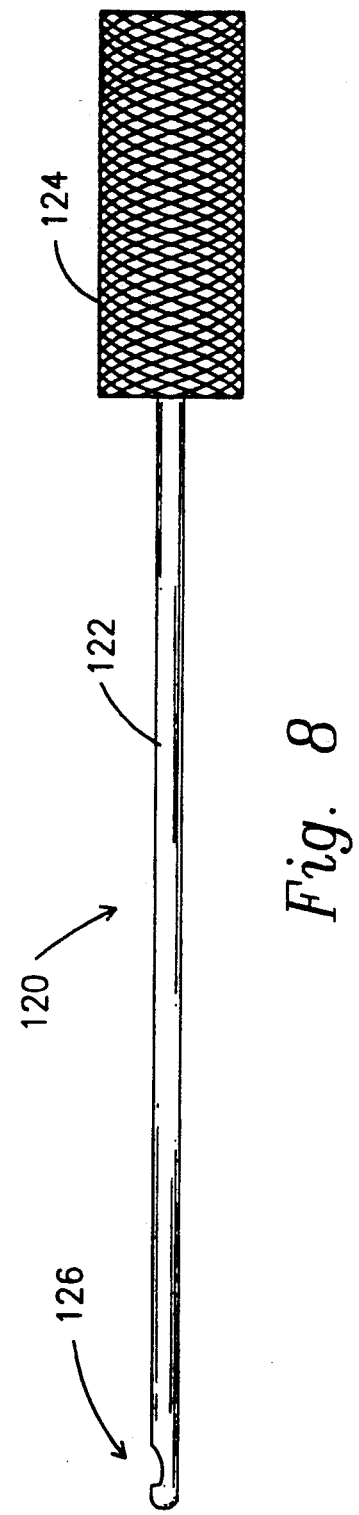
Fig. 7
Fig. 8

CERVICAL DISCECTOMY INSTRUMENTS

TECHNICAL FIELD

This invention relates to arthroscopic surgical instruments. More particularly, it relates to miniature tools having utility in cervical discectomy.

BACKGROUND ART

Neck pain is sometimes caused by the pressure of a ligament bearing against the spinal cord. The pressure can be surgically relieved by debulking, i.e., removing some of the nucleus beneath the ligament so that the ligament can return to its normal position.

Nucleus debulking has heretofore been performed conventionally, i.e., a relatively large incision is made and the surgeon outs through the membrane that overlies the ligament and through the ligament in order to reach the nucleus. The nucleus is out and sufficient amounts thereof are removed to thereby remove the pressure that was the source of the pain.

The tool usually employed to debulk the nucleus is known as a punch tool because it operates something like a paper punch, i.e., a shearing action accomplishes the desired cutting. More particularly, a typical punch tool has an elongate neck and the shearing mechanism is positioned at the distal end of that neck. A pair of handle members at the proximal end of the neck are squeezed by the surgeon and the squeezing action causes a first part of the shearing mechanism to slide with respect to a stationary second part of that mechanism, and nucleus matter between said parts is sheared from the main body of nucleus matter.

The cervical discectomy punches of the type just described operate in a batch mode, i.e., they shear a single piece of tissue for each entry to the surgical site through an incision. After each shearing action, the punch must be withdrawn, an irrigation tool must be inserted to irrigate the site and place the sheared piece of nucleus into suspension, the irrigation tool must be withdrawn, a suction tool must be inserted to vacuum the irrigation fluid and the sheared piece, the suction tool must be withdrawn, and the punch inserted for another shearing action. Thus, a surgeon might be required to make dozens of entries and exits through an incision in the course of a surgical procedure when using a conventional, one bite punch instrument. Such multiple entries, exits, and re-entries obviously extend the time required to perform the surgical procedure, and tire the surgeon and surgical assistants.

It is well known that arthroscopic surgical techniques require much smaller incisions and thus permit much faster patient recovery, thereby reducing the length of hospital stays and saving the expenses associated therewith, but arthroscopic tools capable of performing cervical discectomys do not appear in the prior art.

The prior art, when considered as a whole, neither teaches nor suggests to those of ordinary skill in this field how the conventional punch could be improved, or how the debulking procedure could be performed arthroscopically.

DISCLOSURE OF INVENTION

A novel set of miniature tools is provided for use by arthroscopic surgeons so that cervical discectomy can be performed arthroscopically for the first time.

A first tool enables the physician to properly set a guide wire, known as a K wire after the first initial of its inventor's name, in the nucleus to be debulked. The K wire guides all of the instruments used subsequently in the surgical procedure to the site of the procedure. Heretofore, arthroscopic surgeons had no means for facilitation of K wire insertion between vertebrae.

A second and third tool are provided to facilitate the initial dilation of the arthroscopic incision; moreover, the second tool is the main sheath through which all other tools are inserted throughout the course of the surgical procedure and also serves as the irrigation tool so that the operation site can be irrigated with saline solution as needed.

A fourth tool is a ligament cutter; it is inserted through the bore of the main sheath after the third tool has been removed therefrom and said fourth tool performs the function its name expresses. More particularly, it cuts through the membrane that overlies the ligament and it further cuts a passageway through the ligament to expose the nucleus material thereunder.

The set further includes a novel punch tool having a continuous suction port. The novel punch tool enables the physician to complete an entire debulking procedure, i.e., to perform repeated shearing actions, with a single insertion through an incision. The punch is inserted a single time, and the physician squeezes the handle members thereof as many times as needed so that the shearing members slice off as many pieces of nucleus material as required. The pieces of excised matter are continuously removed from the site by a continuous suction that withdraws irrigation fluid and surgical debris from the site. The suction means is provided in the form of an elongate suction bore that is formed in the neck of the punch; a suction port to which a cannula is releasably secured is positioned at the proximal end of the suction bore, and an opposite end of the cannula is detachably secured to a collection tank that is in fluid communication with a source of negative pressure. Suitable means are provided so that the physician can control the flow rate of the irrigation fluid through the suction bore.

An arthroscopic cervical osteotone, an arthroscopic cervical cureet, a batch-type nucleus extractor, and a second type of cureet are also disclosed; all of these tools are insertable through the main sheath as and if needed. The second type of cureet tool has a handle arrangement like the novel continuous suction punch to facilitate its use.

Thus it is apparent that the primary object of this invention is to provide arthroscopic surgeons with the tools they need to perform cervical discectomys.

A more specific object is to provide a continuous suction punch to facilitate performance of arthroscopic procedures.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 7 is a side elevational view of a novel cervical osteotone member;

FIG. 8 is a side elevational view of a novel cervical cureet;

Similar reference numerals refer to similar parts throughout the several views of the drawings.

BEST MODES FOR CARRYING OUT THE INVENTION

Figure 1:
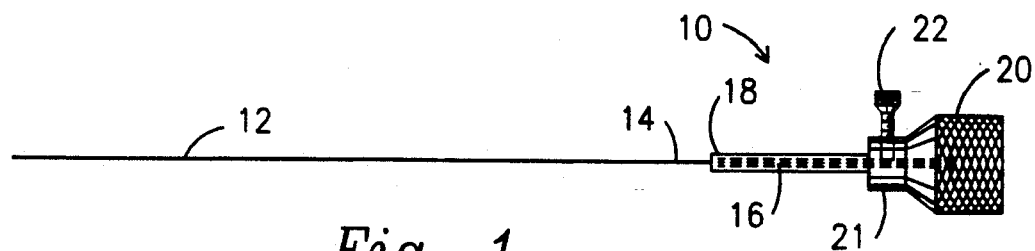
FIG. 1 is a side elevational view of a novel K-wire push knob showing a length of K-wire retained therewithin.

Referring first to FIG. 1, there it will be seen that the novel K wire push knob is denoted 10 as a whole; the K wire is denoted 12. The proximal end 14 of K wire 12 is received within bore 16 that is formed in push knob 10. More particularly, the push knob includes a boss 18 and a knurled base 20; bore 16 extends the entire length of the boss and part of the length of the base as shown. A set screw 22 having a knurled head screw threadedly engages an internally threaded radial bore formed in a reduced diameter part 21 of base 20, said radial bore intersecting bore 16 so that the leading end of the set screw bears against the K wire when the set screw is advanced to releasably retain the guide wire within bore 16.

After the arthroscopic incision has been made, the push knob is grasped by the physician and the distal end of the K wire is inserted into the ligament at the point where the underlying nucleus is to be debulked. The push knob 10 is then removed from the K wire by loosening set screw 22; penetration of the distal end of the K wire into the ligament retains it in position throughout the remainder of the surgical procedure.

K wire 2 is preferably about 140 mm in length, and the overall length of push knob 10 is 24 mm. The reduced diameter part 21 of base 20 is 8 mm in length and the balance of base 20 is 12 mm in length.

Figure 2:
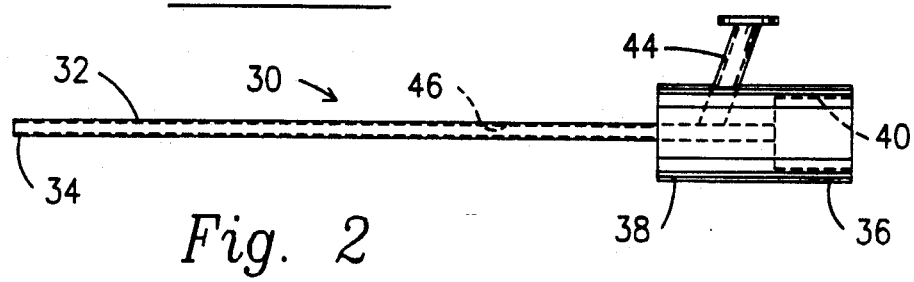
FIG. 2 is a side elevational view of a novel dilator tube having a water port.
Figure 3:
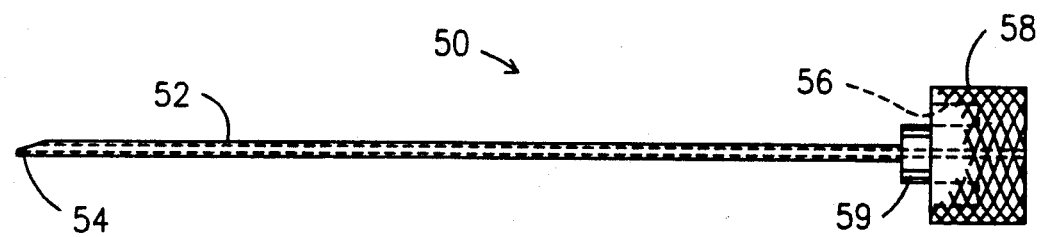
FIG. 3 is a side elevational view of a novel dilator tube.
Figure 4:
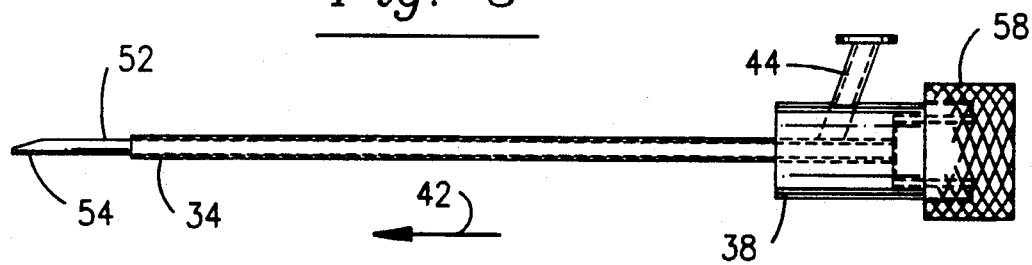
FIG. 4 is a side elevational view showing the tubes of FIGS. 2 and 3 in their assembled configuration.

The incision is then dilated in a novel way. The dilator tube 30 of FIG. 2 and the dilator tube 50 of FIG. 3 are releasably coupled together as a preparatory step to the dilation. Once coupled together, they are threaded over the K wire so that they are properly positioned. More particularly, tubular part 52 of dilator tube 50 is slidably, i.e., telescopically, inserted into the hollow bore of the tubular part 32 of dilator tube 30. The resulting assembly is depicted in FIG. 4 and this assembly is guided to the site by the K wire, i.e., the bore of tubular part 52 axially receives said K wire. Note that the distal end 54 of tubular part 52 is tapered and extends beyond the distal end 34 of tubular part 32. Note further that the proximal end 36 of base 38 of tube 30 is slidably received within circular recess 56 formed in knurled base 58 of tube 50 and that boss 59 of base 58 is slidably received within a complementally formed recess 40 formed in base 38 of tube 30. It should be noted that boss 59 extends from a bottom wall of recess 56. This provides a double look between tubes 30 and 50.

The tapered distal end 54 of tube 50 performs the initial dilation; the taper is provided to avoid tearing the ligament as it passes through. After tube 50 has been advanced, then tube 30 is similarly advanced, i.e., it is advanced to the left as denoted by the directional arrow 42 in FIG. 4. This further dilates the incision.

Tube 30 further includes a water port 44 having an inlet means adapted to be engaged by a cannula, not shown; the opposite end of the cannula is detachably secured to a source of saline solution under positive pressure. Suitable valving means are provided so that the physician can control the flow rate of saline solution to port 44. Port 44 is in open fluid communication with bore 46 of tubular part 32 so that saline solution flowing from the source thereof is delivered to the site of the surgical procedure under the direction and control of the surgeon.

After dilator tube 30 has been advanced as indicated by directional arrow 42 to complete the dilation of the incision, dilator tube 50 is then slidingly decoupled therefrom and withdrawn. Dilator tube 30 is then used as the main sheath through the bore 46 of which other instruments are inserted as the surgical procedure progresses, i.e., main sheath 30 remains in position, as does K wire 12, until the surgical process of debulking the disc is undertaken.

The inside diameter of main sheath 30, i.e., the diameter of bore 46, is 2.5 mm, and the outside diameter of sheath 30 is 3 mm. The overall length of main sheath 30 is 81 mm. The length of tubular part 52 of dilator tube 50 is 92 mm, including the 10 mm length of boss 59. Recess 40 formed in base 38 of main sheath 30 is also 10 mm in depth to receive said boss 59.

Figure 5:
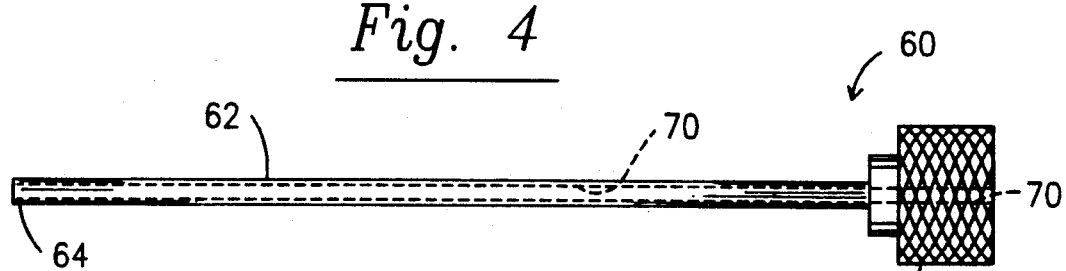
FIG. 5 is a side elevational view of a novel ligament utter.

The ligament cutter 60 of FIG. 5 is next employed; it has an overall length of 104 mm and it includes a tubular part 62, having an outside diameter of 2.4 mm, said tubular part 62 having a leading end 64; leading end 64 has a cookie cutter-style cutting edge. Tool 60 further includes a proximal end having a 10 mm in length knurled base 66, a boss 68 having about the same length, and a bore 70 for receiving the K wire. The ligament cutter 60 is used by threading it onto the K wire, i.e., by aligning said wire with bore 70 at the leading end of the cutter and by advancing the cutter through bore 46 of main sheath 30 toward the surgical site. The physician then oscillates the cutter 60 about its longitudinal axis of rotation as indicated by double-headed directional arrow 72; this action causes cutting edge 64 to slice through the membrane overlying the ligament and continued oscillation and advancement of the cutter enable it to cut a passageway through the ligament and into the underlying nucleus. The cutter and K-wire are withdrawn after the passageway has been formed, but main sheath 30 remains in position.

Figure 6:
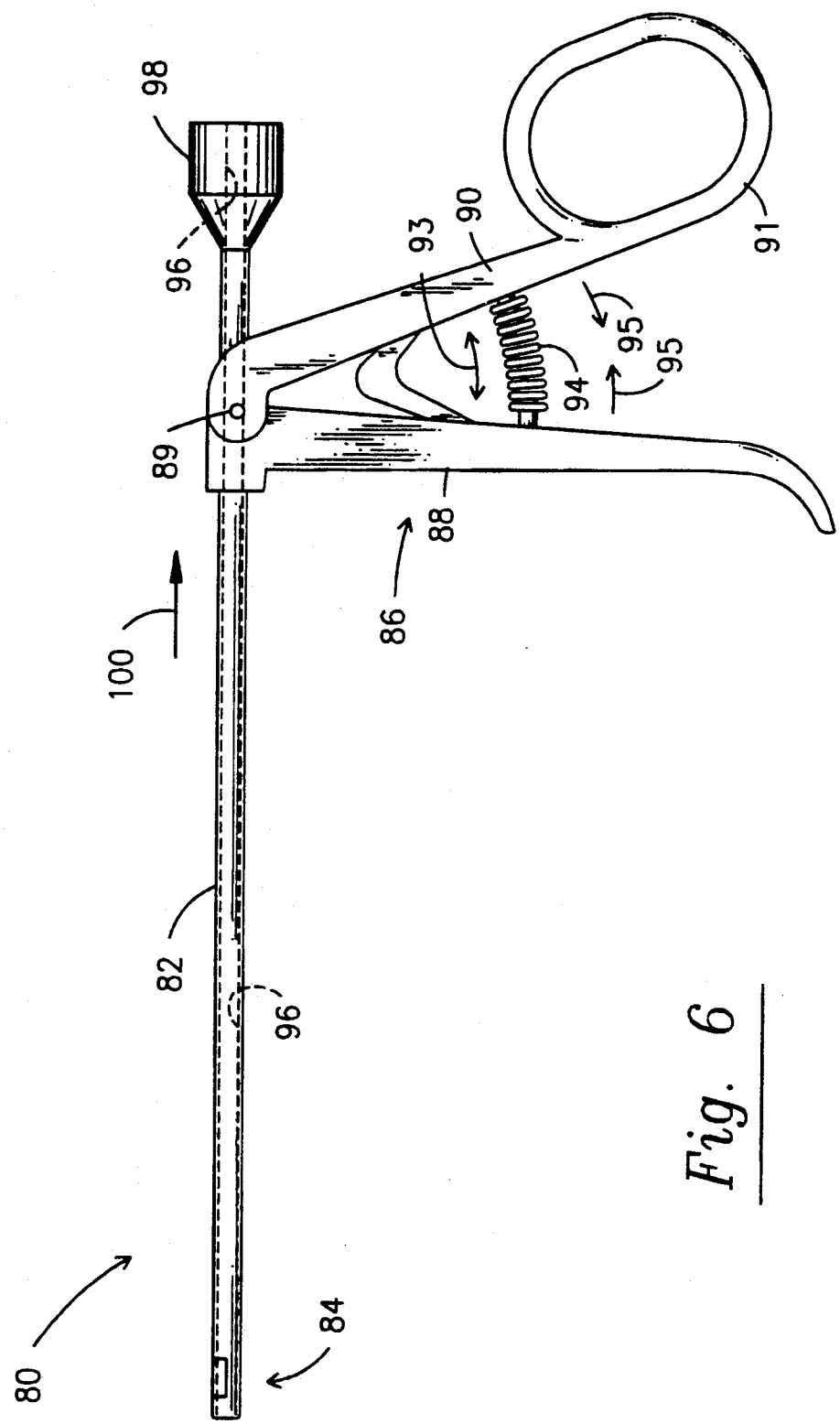
FIG. 6 is a side elevational view of the novel cervical continuous suction punch.

Debulking of the nucleus may now be undertaken; the preferred tool for performing the debulking procedure is depicted in FIG. 6 and is denoted as a whole by the reference numeral 80.

This illustrative embodiment of the novel cervical continuous suction punch 80 includes an elongate neck 82 having a pair of shearing members collectively denoted 84 at the distal end thereof. Shearing members 84 are known in larger punch tools of the type used in conventional, i.e., non-arthroscopic surgery, and thus their construction need not be described. A novel handle means 86 in the form of a pair of handle members 88 and 90 is integrally formed with neck 82 at the proximal end thereof and said handle members depend therefrom; the members are pivotally mounted about pivot point 89, and member 90 has a thumb-receiving loop 91. A strip 92 of spring steel or other suitable material biases handle members 88 and 90 apart from one another as indicated by arrow 93, i.e., the physician must overcome the bias to squeeze said handle members toward one another. Shear members 84 are spaced apart from one another when punch 10 is in repose and ultimately converge toward one another when said handle members are squeezed; a diverging motion precedes the converging motion, but, again, the particular operation of the shearing members is well known and need not be described here.

A coil spring 94 or other suitable bias means is employed to urge the handle members 88 and 90 toward one another as indicated by converging arrows 95; thus, spring steel member 92 and coil spring member 94 are first and second bias means, respectively, that oppose one another. The strength of the opposing bias means is substantially equal. This unique arrangement of parts removes play from the handle means 86 and insures that the handle members 88 and 90 will always return to their respective positions of repose when said handle members are released.

A bore 96 is formed in neck 82 and provides fluid communication between shears 84 and suction port 98 at the proximal end of punch tool 80. Bore 96 extends into port 98 as shown; port 98 provides a mounting means to which a first end of a cannula, not shown, or other suitable flexible tube means is detachably secured when the novel punch 80 is in use. The second end of the cannula is detachably secured to an unillustrated collection receptacle that is in fluid communication with an undepicted source of negative pressure.

The site of the surgical procedure is irrigated during the nucleus-shearing process by causing irrigation fluid to flow into water port 44 in main sheath 30; the inside diameter of the main sheath is sufficient to receive neck 82 of punch tool 80 and to allow sufficient space thereabout to allow the irrigation fluid to flow freely to the surgical site. Thus, as each piece of nucleus is sheared by shears 84, releasing the squeezing motion imparted to handle members 86 and 88 opens the shears and releases the excised pieces into the irrigation fluid.

Suitable means are provided to permit the physician to control the amount of negative pressure supplied to port 98 and thus the flow rate of irrigation fluid and surgical debris flowing therethrough in the direction of arrow 100.

Thus, a single insertion of neck 82 through the bore of main sheath 30 is the only insertion needed to complete the entire debulking procedure. Irrigation fluid is introduced through water port 44 throughout the entire debulking procedure, and the suction applied to port 98 is similarly continuous throughout said procedure.

Neck 82 is preferably about 105 mm in length, exclusive of handle 86; said handle 86 has a length, measured from the neck 82 to the lowermost end of handle member 88, of about 85 mm. The outside diameter of neck 82 is 2.5 mm, and the length of the movable part of the shear members 84 is 4 mm.

FIG. 7 depicts a cervical osteotone 110 that may also be inserted through main sheath 30 if chiseling of a vertebrae is required at any stage of the procedure. Osteotone 110 includes a solid rod 112 having a chisel edge 114 formed in its leading end and a knurled base member 116 fixedly secured to its proximal end. The overall length of osteotone 110 is 125 mm; the length of rod 112 is 105 mm. The lateral extent of chisel edge 114 is 2.3 mm so that the tool is easily insertable through the bore of the main sheath.

A novel cervical cureet or scoop member 120 is depicted in FIG. 8; its rod part 122 and knurled base 124 have the same dimensions as the corresponding parts of the osteotone of FIG. 7. A scoop means 126 is formed in the leading end of rod 122; it has the same construction as a conventional scoop means of the type used in non-arthroscopic surgery, but is only 2.2 mm in length. Cureet 120 is employed to scoop up the bone fragments created by bone chisel 110.

Figure 9:
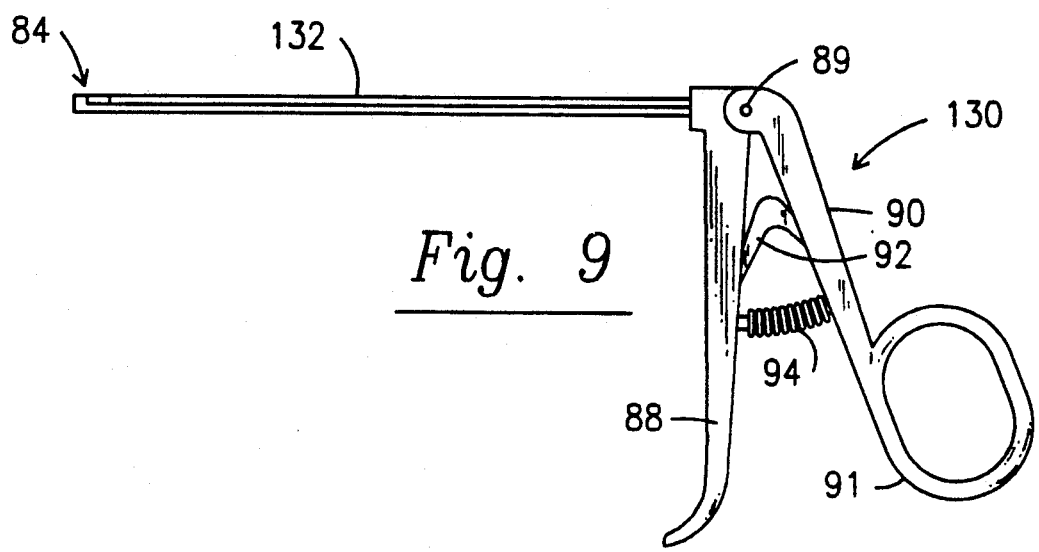
FIG. 9 is a side elevational view of a batch-type punch tool of arthroscopic dimensions that may be employed in lieu of the continuous suction punch of FIG. 6.

The punch tool 130 of FIG. 9 is like the tool of FIG. 6 in all respects except that it lacks suction port 98 and thus does not perform continuous vacuuming of the surgical site. It is suitable for use where the amount of debulking is limited. Neck 132 thereof is 105 mm in length, has an outside diameter of 2.4 mm, but has no bore formed therein; shear members 84 and the rest of the parts are similar to the parts of the punch shown in FIG. 6, as indicated by the common reference numerals.

Figure 10:
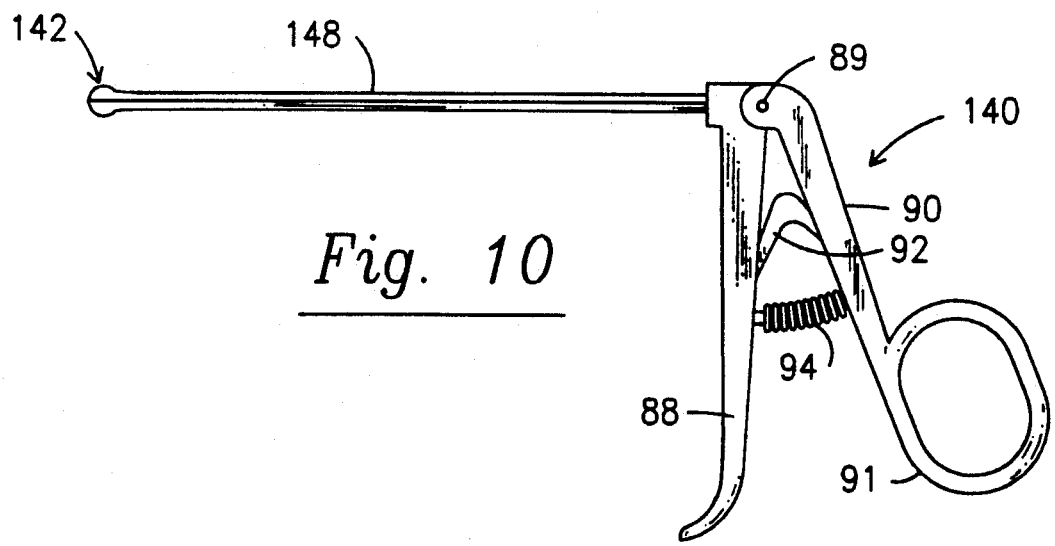
FIG. 10 is a side elevational view a cureet tool having handle members like the handle members of the punch of FIG. 6.

Similarly, the cureet 140 of FIG. 10 has a construction like that of the punch tool of FIG. 9, but it has a distal end with scoop means 142 that is activated by squeezing handles 88 and 90. Its neck 148 is also 105 mm in length and 2.4 mm in outside diameter and it can also be inserted through the bore of main sheath 30.

All of the dimensions disclosed herein are believed to be quite critical although small deviations therefrom still fall within the scope of this important invention. The dimensions allow cervical discectomy to be performed by arthroscopic instruments. The inside and outside diameters of the dilator tubes and the outside diameters of the members insertable through the main sheath 30 are critical because they enable the arthroscopic procedures disclosed herein.

This invention is clearly new and useful. Moreover, it was not obvious to those of ordinary skill in this art at the time it was made, in view of the prior art considered as a whole as required by law.

This invention pioneers the art of arthroscopic cervical discectomy instruments. Accordingly, the claims that follow are entitled to broad interpretation, as a matter of law, to protect from piracy the heart or essence of this breakthrough invention.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, what is claimed is:

1. An arthroscopic tool, comprising:

an elongate tubular neck having a distal end and a proximal end;

a handle means disposed at said proximal end of said elongate tubular neck in depending relation therefrom;

said handle means including a pair of handle members;

said pair of handle members being pivotally mounted to one another at a first end thereof and being spaced apart from one another at a second end thereof when in repose;

a pivot point about which said handle members pivot when an externally applied force is imparted thereto;

an elongate bore formed in said tubular neck, sad elongate bore having a distal end and a proximal end coextensive with the distal end and the proximal end of said elongate tubular neck;

a suction port formed at said proximal end of said elongate bore;

a first bias means for urging said handle members away from one another with a first predetermined level of force;

said first bias means being disposed between the handle members of said pair of handle members;

a second bias means for urging said handle members toward one another with a second predetermined level of force;

said second bias means being disposed between the handle members of said pair of handle members; and said first and second predetermined levels of force being substantially equal to one another;

whereby suction applied to said suction port draws irrigation fluid and surgical debris into said distal end of said elongate bore so that said fluid and debris are continuously vacuumed from a surgical site during a surgical procedure; and whereby said first and second bias means substantially eliminate play between said handle members throughout their entire range of motion; and whereby said handle members are under a substantially constant level of bias throughout said entire range of motion.

2. The tool of claim 1, wherein said first bias means is a strip of spring steel and said second bias means is a coil spring.

3. The tool of claim 2, wherein said first bias means is positioned between said second bias means and said pivot point.

* * * * *